United States Patent [19]

Niekamp et al.

[11] Patent Number: 4,464,204
[45] Date of Patent: Aug. 7, 1984

[54] ALKYLIDENATION OF FRUCTOSE WITH PERFLUORINATED ACID CATALYSTS

[75] Inventors: Carl W. Niekamp, Forsyth; Martin Seidman, Decatur, both of Ill.

[73] Assignee: A. E. Staley Manufacturing Company, Decatur, Ill.

[21] Appl. No.: 445,114

[22] Filed: Nov. 29, 1982

[51] Int. Cl.$^3$ .................... C07H 1/06; C13D 3/14; C13K 11/00
[52] U.S. Cl. .................................. 127/36; 127/42; 127/46.1; 127/46.2; 536/4.1; 536/18.6; 536/124; 536/127
[58] Field of Search ................ 127/36, 46.1, 42, 53, 127/46.2; 536/4.1, 128, 127, 18.6, 124

[56] References Cited

U.S. PATENT DOCUMENTS

| | | | |
|---|---|---|---|
| 2,715,121 | 8/1955 | Glen et al. | 536/4.1 X |
| 2,813,810 | 11/1957 | Smith et al. | 127/55 |
| 2,857,374 | 10/1958 | Baird | 536/124 X |
| 3,607,862 | 9/1971 | Jaffe et al. | 536/124 |
| 3,622,560 | 11/1971 | Hindley et al. | 536/124 |

OTHER PUBLICATIONS

Studies on Glycosides and Isopropylidene Derivatives—Kurt Erne Acta Chemica Scandinavica 9 (1955), 893–901.
Electrolytic Cell Membrane Development Surges—Stephen C. Stinson, C&EN, Mar. 15, 1982, pp. 22–25.

*Primary Examiner*—Kenneth M. Schor
*Attorney, Agent, or Firm*—Forrest L. Collins; Philip L. Bateman; M. Paul Hendrickson

[57] ABSTRACT

Aqueous fructose and aldehydes, ketones and/or acetals may be effectively catalyzed into alkylidene fructose derivatives with immobilized acid catalysts. The reaction provides a means for enriching the fructose content of conventional high fructose corn syrups. Perfluorinated acid resins are especially effective catalysts for converting aqueous fructose and acetone solutions into diacetone fructose. Catalysis with the perfluorinated acid resins may be conducted at significantly lower conversion temperatures with superior reactant and reaction product exchange rates. Enrichment of high fructose corn syrups may be generally accomplished by catalyzing the fructose and acetone into a diacetone fructose solution with the perfluorinated acid resin, allowing the dextrose to precipitate from the diacetone solution, hydrolyzing the diacetone fructose to fructose and recovery of the enriched fructose product therefrom. The water-insoluble catalysts afford a reusable catalyst system which can be easily separated from the processed products. The perfluorinated acid resins produce a high quality, food-grade syrup products essentially free of ash, organoleptic bodies (e.g. flavoring, coloring, etc.) and other objectionable by-product contaminants.

10 Claims, No Drawings

ALKYLIDENATION OF FRUCTOSE WITH PERFLUORINATED ACID CATALYSTS

BACKGROUND OF THE INVENTION

U.S. Pat. No. 2,813,810 by Smith et al. discloses a method for separating glucose and fructose crystals from invert sugar or sucrose. In the Smith et al. method, invert sugar solids were dissolved in water (20 ml) and acetone (400 ml) and then treated with 20 grams of a commercial sulfonated phenol-formaldehyde ion exchange resin. The patentees reported that, after 7 days, the dextrose precipitate and resin were separated from the liquid reactants to provide a supernatant solution of alpha-diisopropylidene-D-fructose. Crystalline fructose was recovered from the supernatant solution by concentrating the supernatant, hydrolyzing the concentrate with a mineral acid, neutralizing the hydrolyzate, dissolving the hydrolyzed concentrate in hot absolute ethanol and cooling the concentrate to provide a crystalline fructose product.

In a paper authored by K. Erne ("Studies of Glycosides and Isopropylidene Derivatives" *Acta Chemica Scandinavica* 9, (1955), pages 893–901) cation exchange resins (sulfonated acid type) were used to catalyze the condensation of acetone with glucose and fructose. Erne reported fructose more readily reacted with acetone to form 1,2-4,5-diisopropylidene-beta-D-fructopyranose than glucose under ambient conditions, but that glucose in boiling acetone produced a 1,2-mono- and alpha-1,2-5,6 diisopropylidene glucofuranose mixture. The sulfonic acid type ion exchange resins were reported to be less effective than strong mineral acids. Substantial inactivation of the resin catalyst and the production of degradative by-products were also observed by Erne.

Fructose is obtainable from a variety of natural products and synthetic processes. The enzymatic modification of sugars provide a particularly attractive source for fructose. Within recent years fructose-containing syrups of about 30% to about 52% fructose content (d.s.b) have been conveniently prepared by isomerizing high dextrose syrup into high fructose syrups with glucose isomerase.

High fructose corn syrups (HFCS) are commercially manufactured by enzymatically isomerizing a high dextrose conversion syrup (which typically contains approximately 4%-8% disaccharides and higher oligosaccharides and 92%-96% dextrose) to fructose. Compositionally a HFCS typically contains from 38%-46% fructose, 48%-54% dextrose, 1%-4% disaccharide and from about 3%-8% saccharides of a D.P.$_3$ or higher. Fructose is sweeter than dextrose. It is conventional to enrich the syrup fructose content (e.g. 55% or higher) by chromatographic fractionation and separation techniques. The enrichment process must necessarily produce a syrup essentially free from organoleptically detectable by-products.

Although considerable research effort has been devoted towards enriching the fructose content of high fructose corn syrups, the earlier work by Smith et al. and Erne is inapplicable to the manufacture of high fructose corn syrups which contain at least 55% or higher fructose. Smith et al. employed dry invert sugar (approximately 50% dextrose and 50% fructose) while Erne utilized a dry monosaccharide (glucose or fructose) dissolved in acetone. The Smith et al. technique required several days (7) to precipitate the dextrose from the diacetone solution while Erne observed substantial degradation of the catalytic resin and reaction product within about 20 hours.

Within recent years, perfluorinated exchange resins with functionally active ionic (e.g. sulfonated and/or carboxylate) groups have gained prominence for a variety of industrial applications. The commercially available perfluorinated ionic membranes are reportedly produced by a variety of chemical processes as disclosed in *C&EN*, Mar. 15, 1982 "Electrolytic cell membrane development surges" by S. C. Stinson, pages 22–25.

Applicants' studies have shown that conventional sulphonated type exchange resins are ineffective for converting HFCS into enriched fructose syrups. This ineffectiveness arises mainly because of certain inherent deficiencies of these conventional sulfonated exchange resins. A HFCS contains a substantial amount of water. In a commercial operation, it is impractical to dehydrate HFCS. Conventional sulfonated resins have a significantly greater affinity for water than acetone. This higher affinity for water tends to load the porous interstices and reactive sites of the resin with a disproportionate concentration of water. The presence of water excesses within the catalytically active sites complicates the efficacy of the acetonation. The catalytic sites are capable of hydrolyzing diacetone fructose to fructose in the presence of excess water. This reversible reaction leads to incomplete catalysis of the fructose to diacetone fructose. High fructose corn syrups also contain significant amounts of saccharide components other than dextrose and fructose. Conventional cation exchange resins tend to absorb and retain an enriched content of the disaccharide and oligosaccharide components of the HFCS. This creates an excessive viscosity for effective mobility of fructose to the catalytic sites and transfer of the diacetone fructose therefrom. This excessive disaccharide and higher saccharide concentration also substantially reduces the level of available fructose. This significantly reduces the amount of fructose and acetone available for catalysis to diacetone fructose. In addition, a substantial portion of the dextrose, fructose and converted diacetone fructose will remain within the porous interstices of the resin, which in turn, reduces the amount of recoverable dextrose precipitate and diacetone fructose.

The inventors unexpectedly discovered that the problems related to the use of HFCS and conventional sulfonated resins could be effectively overcome by conducting the catalysis with a perfluorinated exchange resin. The mobility of the desired (i.e. fructose and acetone) reactants and reaction product from the catalytic active sites was significantly enhanced through the use of the perfluorinated exchange resins. Employing HFCS as a fructose source, these perfluorinated resins provide an exceptionally high interchange rate. The efficacy of the perfluorosulphonated polymeric resins more completely converts the fructose of HFCS into diacetone fructose. By this mode of catalysis, one achieves a higher degree of solution supersaturation. This leads to quicker and more complete precipitation of dextrose from the reaction mixture. The perfluorinated sulfonate resins are very potent catalysts and significantly accelerate the rate of catalysis. The preferential absorbtion of water and oligosaccharides by conventional resins is essentially eliminated through use of the perfluorinated catalyst system. The catalysis substantially reduces the level of undesirable by-products. The perfluorosulphonic acid resins also provide a catalyst system which can be more easily segregated from the processed materials.

DESCRIPTION OF THE INVENTION

According to the present invention, there is provided a method for converting an aqueous solution of a high dextrose and fructose content into a syrup of enriched fructose, said method comprising:

(a) admixing an aqueous fructose and dextrose solution with an effective amount of at least one member selected from the group consisting of aldehyde, ketone and acetal to permit the catalytic conversion of a substantial portion of the fructose into alkylidene fructose;

(b) converting a substantial portion of the fructose within the mixture to an alkylidene fructose by catalysis with perfluorinated acid catalyst;

(c) allowing a substantial portion of the dextrose to precipitate from the converted mixture; and (d) partitioning the precipitated dextrose from the converted mixture to provide a liquid portion of an enriched, alkylidene fructose content.

It has been discovered that perfluorinated cation exchange resins are highly effective catalysts for converting fructose and an aldehyde, ketone and/or acetal into alkylidene fructose. These water-insoluble resins readily catalyze the fructose of high fructose corn syrups (HFCS) and acetone into diacetone fructose. They may also be used to hydrolyze aqueous diacetone fructose solutions to fructose.

The perfluorinated cation exchange resins are typically comprised of a perfluorinated polymeric backbone chain which contains a plurality of appendant acid groups. Illustrative perfluorinated exchange resins may be generally depicted by the polymeric structural formula: $\text{-[(CF}_2\text{CF}_2\text{)}_n\text{C}_2\text{F}_3\text{Q]}_x$ wherein "Q" represents an appendant perfluorinated acid group, "n" is an integer representing the number of tetrafluoroethylene units which intervene between the Q-containing trifluoroethylene units and "x" the number of polymeric acid groups. The appendant Q groups are typically comprised of a perfluorinated ionic moiety represented by the formula $-Q-A^+$, wherein Q' represents a perfluorinated group and $A^+$ represents an acid group. The Q' group will typically consist essentially of a perfluoroorgano moiety connected to the polymeric carbon atom via an oxy or difluoromethylene radical which forms a bridging linkage between the polymeric chain and the acid moiety. The commercially available exchange resins reportedly contain, as Q', either the $-(CF_2)_{2-5}$ and/or $-O-CF_2-CF(CF_3)O(CF_2)_{1-5}$ linking moiety. The acid groups will typically be comprised of hydrogen, oxygen and at least one other atom selected from the group consisting of a Period II element of an atomic weight range of about 10 to about 14 (e.g. boron, carbon, nitrogen) and Period III element of an atomic weight ranging from about 28 to about 32 (e.g. phosphorous, sulfur, etc.). Illustrative acid groups include the sulfonic, carboxylic, phosphonic, phosphorous, phosphoric acids, mixtures thereof and the like. The perfluorinated cation exchange resins containing strong acid moieties (e.g. sulfonic acids) are highly functional catalysts for converting fructose and acetone into 1,2:4,5-di-O-isopropylidene-beta-D-fructopyranose.

A sufficient amount of perfluorinated acid resin should be provided to the reactor for the catalysis of fructose and acetone into diacetone fructose. Relatively small amounts of catalyst (e.g. 50 meq. or lower/fructose mole) to levels in excess of 1,000 meq. or higher may be used for this purpose. Normally a catalyst level of about 100 meq. to about 800 meq. will be sufficient to effectively convert the reactants into diacetone fructose. Advantageously, the amount of catalyst will range from about 150 meq. to about 700 meq. with the preferred catalytic usage level ranging from about 200 meq. to about 400 meq.

The perfluorinated exchange resins can be provided in a form which may be easily segregated from the processing streams and products. If desired, the reactor and/or stirring equipment may be coated with the perfluorinated exchange resin to provide the catalytic source for the acetonation reaction. Alternatively they may be used sheeted, fragmented, granulated or beaded catalyst of a dimensional size to permit their segregation from either the diacetone fructose solids or dextrose precipitate. The catalytic reaction may be adapted to batch, semi-continuous and continuous reactor systems. The catalyst system is particularly suitable for a continuous process. In a continuous operation, the acetone and HFCS solution may be continuously fed and passed through a single or plurality of fixed beds containing the immobilized perfluorosulfonic acid resin or reactors impregnated or coated with the resin. The solution flow rate and reaction temperature may be suitably monitored to optimize the conversion to diacetone fructose. Cooling means, crystallizers or hold tanks, may be adapted to the operation to facilitate the precipitation of dextrose from the concentrated diacetone fructose solutions. The continuous operation may also be equipped with means to recycle the acetone and dextrose to the catalytic converter.

A variety of fructose-containing syrups may serve as a fructose source. The extent of fructose enrichment will depend primarily upon the fructose and dextrose content of the fructose-containing syrup. Dextrose and fructose should ordinarily comprise the major dry solids constituents (d.s. by weight basis) of the fructose source material. The dextrose and fructose will advantageously comprise at least 80% and preferably at least 90% by weight of the total dry syrup solids weight. The weight ratio of fructose and dextrose will typically range from about 1:2 to about 2:1 and advantageously within about 2:3 to about 3:2 range. Fructose-containing syrups obtained through enzymatic modification of sugars (particularly the isomerization of dextrose syrups with glucose isomerase), will normally contain an appropriate dextrose and fructose content for use herein. Fructose syrups of about 30% to about 55%, especially commercially available high fructose corn syrups of about 38%-46% fructose content (d.s.b), are an excellent fructose source material for the acetonation.

Although the catalysis of aqueous fructose solutions into alkylidene fructose generally applies to ketones (e.g. acetone, methyl ethyl ketone, diethyl ketone, methyl propyl ketone, cyclohexanone, mixtures thereof and the like), aldhydes (e.g. propionaldehyde, butyraldehyde, mixtures thereof and the like) and acetals (e.g. 2,2-dimethoxypropane, 2,2-diethoxypropane, acetaldehyde diethyl acetal and acetaldehyde dimethyl acetal, mixtures thereof and the like) it is, particularly well suited for the catalytic conversion of acetone and fructose into diacetone fructose. The acetone level is monitored for effective conversion of the fructose to diacetone fructose. Sufficient acetone should be added to the converter to compensate for water contributed by the HFCS and to prevent hydrolysis of the diacetone fructose to fructose. The acetonation normally requires at last 2 moles of acetone for each fructose mole. In a commercial operation, the reactor will most appropriately be provided with at least 5 moles of acetone and advantageously at least 10 moles of acetone for each mole of fructose. Substantially greater molar excesses of acetone (e.g. 200 moles or higher) may be used but are generally avoided due to added equipment and acetone recovery expenses. Advantageously, the acetone level will rage from about 15 moles to less than about 100 moles for each fructose mole and preferably from about 20 moles to about 25 moles of acetone/fructose mole.

The catalytic efficacy of the perfluorinated acid resins is not adversely affected by the presence amounts of water. Fructose syrups which contain from about 10% to about 80% by weight water or higher may be adapted to the process. When high fructose corn syrups are utilized as the fructose source material, the feed syrup water content will advantageously range from about 20% to about 60% of the total syrup weight and most advantageously about 25% to about 35% by weight water. These ranges typify the water content of syrups normally discharged from the isomerization columns. Within these operational parameters, the reactor will generally be provided with a reaction media which contains less than about 1 mole water for each acetone mole. Advantageously, the molar proportion of acetone to water will range from about 1 mole to about 10 moles acetone for each water mole with particularly effective results being obtained at about a 3:2 to about 4:1 (most preferably at about 2:1) acetone to water molar ratio.

The reaction temperature and time intervals are suitably regulated so as to convert the reactants into diacetone fructose. The most appropriate temperature and contact time will depend to a large extent upon the type of reactor used for the conversion. In a continuous operation, shorter reaction times may be combined with higher temperatures so as to inhibit the formation of fructose degradative by-products. The conversion time interval may be appropriately controlled by regulating the flow rate of reactants through the reactor. Longer reaction periods may be effectively used in batch or continuous reactors by reducing the reaction temperature.

For most operations, the catalytic conversion will be conducted at a temperature of less than about 50° C. with further improvements in product quality and production rates being accomplished at conversion temperatures of less than 35° C. These reduced operational temperatures minimize the formation of mono- and diacetone glucose, and other undesirable by-products. The catalytic conversion of the reactants into diacetone fructose will proceed more rapidly than the rate of dextrose precipitation. However, the lower conversion temperatures will reduce the total time needed for effective recovery of crystalline dextrose from the diacetone fructose solution. The catalytic converting temperature is advantageously maintained within about 10° C. to about 25° C. range and most preferably from about 15° C. to about 20° C. Substantially complete catalysis of the reactants into diacetone fructose can generally be effectuated within less than about a day (e.g. about half-hour to about 24 hours). More typically, the catalysis can be completed within about 2 hours to about 20 hours and most typically within about 5 hours to about 15 hours. The reaction temperatures may be controlled to optimize the crystallization of the dextrose. For example, more elevated converting temperatures may be used to accelerate the rate of catalysis with lower converting temperatures being employed in the later stages of the catalysis to facilitate the dextrose crystallization.

The present method provides a means for more effectively converting fructose to diacetone fructose. More highly concentrated diacetone fructose solutions are achievable under the present invention. The more highly concentrated diacetone solutions permit more dextrose to be precipitated from the reaction mixture which, in turn, significantly enriches the diacetone fructose solution content. The method avoids the water dilution requirements, water removal and auxiliary equipment costs of conventional chromatographic separation processes. The catalytic reaction minimizes the production of adverse by-products and organoleptically objectionable bodies. Unlike conventional exchange resins which absorbtively and tenaciously retain a substantial amount of water and reaction product, the polymeric resins used herein retain only a trace amount of the reactants and desired reaction product. The acetonation proceeds at a substantially faster rate and at significantly lower temperatures than conventional catalysis. The ability to catalytically convert the reactants at low operative temperatures permits dextrose crystallites to simultaneously develop and form during the catalysis of the fructose and acetone to diacetone fructose. This should be contrasted with the prior methods which typically require the catalysis to be conducted at temperatures substantially above the dextrose crystallization temperature and a separate cooling step to precipitate the dextrose from the diacetone fructose solution.

There are two isomeric forms of diacetone fructose. The kinetically controlled reaction conditions herein favor the formation of the 1,2:4,5-di-O-isopropylidene-beta-D-fructopyranose isomer instead of the thermally stable 2,3:4,5 beta-D-fructopyranose isomeric form. The reduced conversion temperature coupled with catalytic activity of the perfluorinated sulfonic acid resins of this invention affords a means for providing a diacetone fructose reaction product in the 1,2:4,5 isomeric form and substantially free from the 2,3:4,5 isomer. This will provide a diacetone fructose solution which can be easily hydrolyzed into fructose while minimizing the formation of objectionable organoleptically flavor, color and odorous by-products.

After converting the fructose to the desired solution concentration of diacetone fructose, the dextrose is allowed to precipitate from the solution. In general, catalytic conversion and precipitation of the dextrose may be accomplished within a total time interval ranging from about a half-day or less to about 4 days. Although recoverable dextrose precipitate may be obtained at temperatures in excess of 30° C., it is advantageous to cool the reaction product to a temperature of less than about 25° C. (e.g. 5° C.–20° C.) and preferably about 10° C. to about 18° C. Cooling provides a supersaturated dextrose solution and accelerates the rate at which dextrose precipitates from the diacetone fructose reaction solution.

The dextrose precipitate may conveniently be recovered from the diacetone fructose solution by conventional means such as by filtration, centrifugation, decantation, etc. If desired, the dextrose recovery may be facilitated by progressively decreasing temperatures with or without intermittent removal of dextrose precipitate therefrom. Similarly, the diacetone fructose solution may be concentrated by conventional techniques to further accelerate the rate of dextrose precipitation. Through effective cooling, the total time interval for dextrose recovery from initial star-up may be reduced to less than about 2 days (e.g. about 15 hours to about 50 hours) and most typically within about 20 hours to about 35 hours interval.

In general, the partitioning step will remove more than about 40% by weight of the total dextrose content of the diacetone fructose solution and advantageously a major weight portion. In a typical operation, from about 60 to about 95 weight percent of the total dextrose content of the diacetone fructose solution and advantageously from about 70 to about 90 weight percent will be recovered by the partitioning step herein.

The catalytic hydrolysis of diacetone fructose to fructose is a reversible reaction. The hydrolysis reaction is generally favored by providing a sufficient amount of water to the hydrolyzing medium to shift the equilibrium towards fructose production. Catalytic reconversion of the fructose and acetone into diacetone fructose will generally be inhibited by maintaining the molar ratio of water to total acetone (free and chemically combined) during the hydrolysis reaction at a level in excess of about 11:10 and advantageously at a level of more than about 2:1 moles water for each mole acetone. Further excesses of water (e.g. 30 moles or higher) may be used but are generally unnecessary and undesirable due to additional processing and equipment needed to remove excess water and place the recovered fructose in a marketable form. In a commercial operation, more effective and complete hydrolysis of the diacetone fructose will be obtained by generally maintaining the water level at least about 3 moles and preferably in excess of 10 moles for each acetone mole. During the hydrolysis, the free acetone is advantageously removed from the hydrolyzing medium (e.g. evaporating under a vacuum) as it is formed by the hydrolyzing reaction. Removal of the free acetone during the hydrolysis contributes towards move complete hydrolysis of the diacetone fructose into fructose.

In the manufacture of enriched fructose syrups of a 55% or higher fructose content, the hydrolyzing medium will more typically contain about 2 to about 50 moles water per fructose mole and advantageously from about 4 to about 30 moles water for each fructose mole. If desired, the water content of the reaction product may be adjusted to more closely approximate that of the desired syrup end- product. By maintaining the free acetone level during the hydrolysis at less than about 2 moles acetone (preferably less than 1 mole) for each five moles of water, substantially complete catalytic conversion of the diacetone fructose into fructose may be accomplished.

The aqueous diacetone fructose is hydrolyzed by acid catalysis. Although conventional strong mineral or organic acids may be used to hydrolyze the diacetone fructose to fructose, acid ion exchange resins have been found to yield an unexpectedly superior food-grade hydrolyzate product. The perfluorinated exchange resins mentioned hereinbefore are especially well suited for this purpose. They may be utilized in the hydrolysis of diacetone fructose to fructose at substantially lower temperatures and catalytic concentrations than conventional acids. Enriched fructose products which rely upon perfluorinated acid catalysts to hydrolyze the diacetone fructose to fructose have been found to be essentially free from organoleptic and other objectionable by-products (e.g. color, flavor, degradative, etc. bodies).

Relatively small amounts of catalyst (e.g. 1 meq./fructose mole or less) to levels in excess of 1,000 meq. or higher may be used to hydrolyze the diacetone fructose to fructose. The most appropriate catalytic amount will primarily depend upon the efficacy of the particular catalyst which is used for the hydrolysis. Normally a catalyst level ranging from about 2 meq. to about 800 meq. will suffice for this purpose. Advantageously, the amount of catalyst will range from about 5 meq. to about 700 meq. with the preferred catalytic amount level ranging from about 10 meq. to 400 meq. For the perfluorosulfonic acid resin, it is advantageous to use less than 20 meq. in the hydrolysis.

Although relatively high temperatures (e.g. 80° C. or more) for short time intervals (e.g. one hour or more) may be used to hydrolyze the diacetone fructose to fructose for those applications in which by-product residues are unimportant, it is advantageous for food grade syrups to conduct the hydrolysis at a temperature of less than about 70° C. A hydrolyzing temperature of about 20° C. to about 65° C. (preferably from about 50° C. to about 60° C.) for about 2 hours to about 10 hours (preferably from about 2 hours to about 3 hours) are particularly effective for converting diacetone fructose solution into food-grade, enriched fructose syrups.

Upon completion of the diacetone fructose hydrolysis, the immobilized catalyst (if present) may be removed from the hydrolyzed solution. The hydrolyzing acid exchange resins can be easily separated from the hydrolyzed product by providing the catalyst in a form similar to that used for the catalysis of fructose and acetone into diacetone fructose. The hydrolyzate may be adjusted, if necessary, with an appropriate acid to about pH 3 to about pH 5 (preferably from about pH 3 to about pH 4). Any acetone residue may be removed from the hydrolyzate by conventional techniques such as by distillation, evaporation, etc. Pursuant to the present process, syrups of an enriched fructose content of at least 55% (e.g. 55%-95% or higher fructose content) and preferably of a fructose content of about 60% to about 90% may be easily prepared from 38%-46% HFCS. Notwithstanding the high fructose content, the acid hydrolysis produces an enriched fructose syrup product substantially free from objectionable flavoring and coloring bodies. This substantially reduces the carbon, cationic and anionic exchange resin requirements for placing these syrups in a marketable condition for food applications. The immobilized catalysts provide syrups essentially free from ash residues which normally arise from salts formed by neutralizing water-soluble acid catalyst with a base.

The following examples are illustrative of the invention.

EXAMPLE 1

This example illustrates the use of a perfluorinated sulfonic acid resin[1] to prepare a 75% fructose syrup from 40.4% HFCS[2]. The reaction medium was prepared by adding 900 ml. of acetone of 68.2 grams of 40.4% high fructose syrup. The reaction medium and solid catalyst (112 square inches of the perfluorinated sulfonic acid membrane—14 meq.) were stirred at 24°–25° C. for 45 hours. Under these acetonation conditions, the fructose was converted to 1,2:4,5-di-O-isopropylidene-beta-D-fructopyranose with a substantial portion of the dextrose being precipitated from the liquid solution. The membrane was then removed and the dextrose precipitate was filtered (Whatman No. 2 paper) from the single liquid phase. Saccharide analysis by high pressure liquid chromatography (HPLC) of the unwashed precipitate revealed that the precipitate consisted of 74.3% dextrose, 18.6% fructose and a balance (7.1%) primarily of D.P.$_2$ and higher sugars. Analysis of the liquid phase by HPLC indicated it contained 24.0% dextrose, 29.9% fructose, 44.7% diacetone fructose (86.4% by weight being 1,2:4,5-di-O-isopropylidene-beta-D-fructopyranose) and the balance (1.4%) being comprised of D.P.$_2$ and higher saccharides. Substantially all of the unreacted acetone was then removed from the liquid phase by aspirating with water vacuum in a rotary evaporator in a 60° C. water bath for about 20 minutes. The evaporated syrup (28% solids) was then heated to 65° C. for 2 hours in the presence of 6.3 sq. in. of the perfluorinated sulfonic acid catalyst (0.8 meq.) to hydrolyze the diacetone fructose to fructose. The acetone generated by the hydrolysis was continuously removed by the above rotary evaporating conditions to provide a 50% by weight dry solids syrup product. Analysis of the hydrolyzed product by high pressure liquid chromatography indicated it contained 74.3% fructose and 22.5% dextrose with the balance (3.2%) being primarily comprised of di- and higher HFCS saccharide components.

[1] Nafion 125—A copolymer of tetrachloroethylene perfluoro-3:6-dioxa 4-methyl-7-octensulfonic acid membrane manufactured and distributed by E. I. du Pont de Nemours & Co., Wilmington, Del. 19898
[2] 40.4% fructose, 55.3% dextrose, 2.6% maltose and isomaltose and 1.7% by weight saccharide of D.P.$_3$ and higher The unrefined, enriched fructose syrup (23.2 grams), which contained 50% by weight dry solids, was blended with sufficient 40% high fructose corn syrup[2] (50% d.s.) to provide an enriched fructose syrup containing 55% by weight (d.s.b.) fructose content. The blended 55% high fructose corn syrup (pH 3.5) was then treated with powdered corn (3% by weight of 55% HFCS dry solids weight) for 30 minutes at 60° C. and filtered through Whatman No. 2 filter paper. The carbon-treated filtrate was then ion exchanged (40° C.) through a pair of cation and anion exchange columns. The syrup effluent of a dry substance in excess of 20% by weight solids was collected, adjusted to a pH 3.5, and concentrated under aspirating vacuum (water) in a rotary evaporator immersed in a 60° C. water bath to a 78% dry solids syrup. When evaluated by an expert syrup flavor panel, the 55% high fructose corn syrup received an average flavor grade rating of 8.5±0.5 (1-10 basis). The syrup was characterized as being a colorless, bland, sweet-tasting syrup essentially free from other flavor principles. The flavor rating exceeded those typically obtained from conventional 55% HFCS.

EXAMPLE 2

Example 1 was generally repeated except for the replacement of the perfluorinated sulfonic acid catalyst with conventional acid ion exchange resin. The acetonation reaction was conducted by mixing 100 grams (d.s.) of the styrene/divinylbenzene sulfonic acid exchange resin (Dowex 50WX1-100 (50–100 mesh)) with 1187 grams of acetone and 694 grams of high fructose corn syrup for 21 hours at 26° C. and an additional 22 hours at 18° C. The decrease in catalytic temperature to 18° C. was designed to optimize the rate of dextrose precipitation from the diacetone fructose solution. The dextrose precipitate was separated by filtrating (Whatman No. 2 filter paper) at 18° C. The catalytic resin was removed by sieving through a 200 mesh screen (U.S. Series), washed with water and the washings combined with the liquid diacetone fructose filtrate. Due to attrition of the resin and the substantial amount of absorbed material retained by the resin considerable more difficulty was encountered in attempting to separate the resin from the dextrose precipitate and absorbed substances.

The aceonte was evaporated from the filtrate by aspirating with a rotary evaporator maintained at 40° C. The HPLC analysis of the dextrose precipitate for saccharide revealed that the dextrose precipitate contained 91.2% dextrose, 7.2% fructose and 1.6% D.P.$_2$ and higher saccharides. An HPLC analysis of the filtrate revealed (on a total dry solids weight basis) 10.7% diacetone fructose, 35.0% dextrose and 44.9% fructose. The level of fructose by-products was also higher than that obtained for the perfluorinated sulfonic acid membrane used for the acetonation.

In the regeneration of the diacetone fructose to fructose, 650 ml. of the concentrated filtrate syrup (34% dry solids) was treated with 3 grams (dry substance basis) Dowex 50WX4-200 for 3 hours at 45°–85° C. After the catalyst was separated by filtration, the acetone generated by the diacetone fructose hydrolysis was removed from the filtrate (as described hereinbefore) to provide a 46.5% dry substance fructose syrup which, upon HPLC analysis, revealed a saccharide distribution (on a total dry substance weight basis) of 57.8% fructose, 35.8% dextrose and 6.4% D.P.$_2$ and higher saccharides.

By comparing the Example 1 and 2 results, it will be observed that the perfluorinated sulfonic acid catalyst was substantially more effective in catalyzing a high fructose corn syrup into diacetone fructose. This is evident by comparing the enrichment of the 40.4% fructose content of the high fructose corn syrup to 75% by weight fructose as opposed to the 57.8% fructose content for the Dowex 50WX1-100 catalysis. The perfluorinated sulfonic acid membrane which was removed upon completion of the fructose to diacetone fructose was essentially free from absorbed materials. In contrast, the Dowex WX1-100 contained substantial amounts of absorbed water and other reaction media contaminants which is believed to significantly reduce its efficacy as an acid catalyst. The perfluorinated sulfonic acid catalyst was easily separated from the dextrose precipitate while considerable difficulty was encountered in the separation of the Dowex 50WX1-100 acid catalyst from the dextrose precipitate. The level of perfluorinated sulfonic acid (i.e. 200 meq.H+/fructose mole) to catalyze the fructose to diacetone fructose conversion was substantially less than the 450 meq. level of Dowex 50WX1-100 used in Example 2.

Complete hydrolysis with the perfluorinated sulfonic acid resin of Example 1 was accomplished with about 0.01–0.02 meq. H+/DAF mole within about 2 hours. In contrast, diacetone fructose hydrolysis with the styrene/vinylbenzene acid exchange resin will typically require more catalyst (e.g. about 0.3–1.4 meq. H+/mole diacetone fructose) and time (about 2–4 hours) to completely hydrolyze the diacetone fructose to fructose. The hydrolyzate of this example with the styrene/vinylbenzene acid exchange yields a slightly discolored solution in contrast to the clear solution obtained in Example 1 with the perfluorinated sulfonic acid resin.

What is claimed is:

1. A method for converting an aqueous solution of a high dextrose and fructose content into a syrup of enriched fructose, said method comprising:
   (a) providing an aqueous fructose and dextrose solution comprising at least 80% of dextrose plus fructose on a total dry syrup solids weight basis, wherein the weight ratio of fructose to dextrose ranges from about 1:2 to about 2:1;
   (b) admixing the provided solution with an effective amount of at least one member selected from the group consisting of aldehyde, ketone and acetal to permit the catalytic conversion of a substantial portion of the fructose into an alkylidene fructose;
   (c) converting a substantial portion of the fructose within the mixture to an alkylidene fructose by catalysis with perfluorinated acid exchange resin catalyst;
   (d) precipitating a substantial portion of the dextrose from the converted mixture; and
   (e) separating the precipitated dextrose from the converted mixture to provide a liquid portion of an enriched, alkylidene fructose content.

2. The method according to claim 1 wherein the member consists essentially of acetone, the fructose and acetone are catalytically converted into diacetone fructose, the diacetone fructose of the liquid portion is hydrolyzed into fructose and a syrup of an enriched fructose content is recovered from the partitioned liquid portion.

3. The method according to claim 2 wherein the catalysis of step (c) with the perfluorinated acid catalyst is conducted at a temperature of less than 35° C.

4. The method according to claim 2 wherein the perfluorinated acid catalyst comprises a perfluorinated sulfonic acid catalyst.

5. The method according to claim 3 wherein the aqueous solution contains on a total dry solids weight basis at least 80% by weight dextrose and fructose and the molar weight ratio of dextrose to fructose ranges from about 2:3 to about 3:2.

6. The method according to claim 5 wherein the aqueous solution of dextrose and fructose consists essentially of high fructose corn syrup which contains on a total syrup weight basis from about 20% to about 60% by weight water.

7. The method according to claim 6 wherein the perfluorinated acid catalyst comprises a perfluorinated sulfonic acid catalyst, the catalysis of the fructose and acetone into diacetone fructose is conducted at a temperature ranging from about 10° C. to about 25° C. and the high fructose corn syrup contains, on a total dry solids weight basis, at least 90% by weight dextrose and fructose.

8. The method according to claim 7 wherein for each mole of fructose the catalyst amount ranges from about 100 to about 800 meq. and the amount of acetone ranges from about 15 to about 100 moles.

9. The method according to claim 6 wherein a major weight portion of the total dextrose content within the converted mixture is partitioned from the liquid portion and the diacetone fructose of the partitioned liquid portion is hydrolyzed to fructose with an immobilized acid catalyst.

10. The method according to claim 9 wherein the immobilized acid catalyst consists essentially of perfluorinated acid catalyst.

* * * * *

UNITED STATES PATENT AND TRADEMARK OFFICE
CERTIFICATE OF CORRECTION

PATENT NO. : 4,464,204
DATED : August 7, 1984
INVENTOR(S) : Carl W. Niekamp et al It is certified that error appears in the above-identified patent and that said Letters Patent are hereby corrected as shown below:

Column 4, Line 29, for "hold" read ---holding---
Column 5, Line 11, for "rage" read ---range---
Column 5, Line 15, for "presence" read ---presence of substantial---
Column 7, Line 5, for "star-up" read ---start up---
Column 8, Line 62, for "of 68.2" read ---to 68.2---
Column 9, Line 38, for "powdered corn" read ---powdered carbon---
Column 10, Line 9, for "aceonte" read ---acetone---

Signed and Sealed this

Seventh Day of January 1986

[SEAL]

Attest:

DONALD J. QUIGG

Attesting Officer  Commissioner of Patents and Trademarks